United States Patent
Aljazaeri et al.

(10) Patent No.: US 12,036,075 B1
(45) Date of Patent: Jul. 16, 2024

(54) STERNAL COMPASS

(71) Applicant: KING SAUD UNIVERSITY, Riyadh (SA)

(72) Inventors: Ayman Hassan Aljazaeri, Riyadh (SA); Rakan Ibrahim Nazer, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 18/388,096

(22) Filed: Nov. 8, 2023

(51) Int. Cl.
  *A61B 17/17* (2006.01)
  *A61B 90/00* (2016.01)

(52) U.S. Cl.
  CPC ...... *A61B 90/39* (2016.02); *A61B 2090/3937* (2016.02)

(58) Field of Classification Search
  CPC ............ A61B 17/1728; A61B 17/1725; A61B 17/1721; A61B 17/1732; A61B 17/1739; A61B 17/1792; A61B 17/1789; A61B 17/17; A61B 17/1697; A61B 17/1655; A61B 17/1657; A61B 17/1662; A61B 17/1693; A61B 17/1691
  See application file for complete search history.

(56) References Cited

U.S. PATENT DOCUMENTS

| | | | | |
|---|---|---|---|---|
| 2009/0299416 A1* | 12/2009 | Hanni | ..................... | A61B 17/17 606/103 |
| 2012/0197291 A1* | 8/2012 | Tsai | ................... | A61B 17/2812 606/205 |
| 2017/0181757 A1* | 6/2017 | Viola | ..................... | A61B 17/17 |
| 2019/0105087 A1* | 4/2019 | Sommers | ............... | A61B 17/88 |

FOREIGN PATENT DOCUMENTS

| | | | |
|---|---|---|---|
| IN | 304636 B | | 11/2008 |
| JP | 2010200838 A | * | 9/2010 |

* cited by examiner

*Primary Examiner* — Eduardo C Robert
*Assistant Examiner* — Michelle C Eckman
(74) *Attorney, Agent, or Firm* — Nath, Goldberg & Meyer; Joshua B. Goldberg

(57) ABSTRACT

A sternal compass includes a first scissor clamp arm having a first scissor clamp arm handle end and a first scissor clamp arm effector end; and a second scissor clamp arm having a second scissor clamp arm handle end and second scissor clamp arm effector end. The second scissor clamp arm crosses the first scissor clamp arm at a pivot point. A centerline alignment mechanism is located between the first scissor clamp arm and the second scissor clamp arm. The centerline alignment mechanism has a hinge point aligned with the pivot point. A center line frame extends in line with the hinge point and the pivot point toward the first scissor clamp arm effector end and the second scissor clamp arm effector end. The center line frame has a marking device to mark a centerline of a sternum of a patient.

10 Claims, 3 Drawing Sheets

STERNAL COMPASS

BACKGROUND

1. Field

The present disclosure relates to a sternotomy procedure in which the sternum is cut in two to access the mediastinal cavity for surgeries such as coronary artery bypass surgeries, heart valve surgeries, thoracic aorta and heart transplant surgeries, and particularly to a device for marking the sternum.

2. Description of the Related Art

A sternotomy is considered to be the gold standard incision in cardiac surgery, resulting in low failure rates and excellent proven long-term outcomes. Every year 700,000 median sternotomies are performed in the US alone. A sternotomy is a procedure in which the sternum is cut in two to access the mediastinal cavity for surgeries such as coronary artery bypass surgeries, heart valve surgeries, thoracic aorta and heart transplant surgeries. The procedure is currently performed by a surgeon manually feeling for certain features at the top and sides of the bone to approximate the midline, along which a line is marked. Then this line is manually followed with an electric/pneumatic reciprocating saw to divide the bone in two equal halves. Once the main surgery is complete, steel wires are wrapped around the bone and tightened to pull the two halves back together for healing.

SUMMARY

There are many issues that exist with sternotomies as the identification of the correct landmarks for the sternal midline can sometimes be challenging, especially in emergency situations or with obese subjects. Surgeons, particularly beginners, can easily deviate from the midline resulting in a non-linear or asymmetric cut profile which can lead to grave consequences that would impair proper healing, resulting in issues such as sternal fracture, mechanical instability, and deep sternal wound infection which are all considered serious outcomes. Uneven sternal split could leave one side of the sternum with narrow and weak sternal bone tissue causing closure wires to cut through this narrow segment in what is known as the cheese cutter effect, leading to sternal dehiscence and preventing proper healing.

A sternal compass is a hand-held device that is used by a surgeon, once a sternal bone in exposed, to identify and mark the sternal midline. The device has a clamp-like handle that can control two distal centralizing limbs that function to centralize a marker mechanism.

In one embodiment, a sternal compass includes a first scissor clamp arm having a first scissor clamp arm handle end and a first scissor clamp arm effector end; and a second scissor clamp arm having a second scissor clamp arm handle end and second scissor clamp arm effector end. The second scissor clamp arm crosses the first scissor clamp arm at a pivot point. A centerline alignment mechanism is located between the first scissor clamp arm and the second scissor clamp arm. The centerline alignment mechanism has a hinge point aligned with the pivot point. A centerline frame extends in line with the hinge point and the pivot point toward the first scissor clamp arm effector end and the second scissor clamp arm effector end. The centerline frame has a marking device to mark a centerline of a sternum.

The sternal compass further includes a finger rest cum centerline guide wherein the centerline frame slides within the finger rest cum centerline guide. The finger rest cum centerline guide is attached to the pivot point.

The centerline frame is connected to the hinge point.

The sternal compass further includes a ratchet lock located between the first scissor clamp arm handle end and the second scissor clamp arm handle end.

The sternal compass further includes a stopper located between the first scissor claim arm handle end and the second scissor clamp arm handle end.

The first scissor clamp arm effector end includes a first pinching gripper edge and the second scissor clamp arm effector end includes a second pinching gripper edge.

The sternal compass further includes a first depth limiting protrusion located on the first scissor clamp arm effector end above the first pinching gripper edge, and a second depth limiting protrusion located on the second scissor clamp arm effector end above the second pinching gripper edge. The first depth limiting protrusion and the second depth limiting protrusion prevent the sternal compass from getting below a sternum of a patient to protect internal organs of the patient.

The marking device includes a collet marker holder.

The marking device, in another embodiment, includes a first collet marker holder and a second collet marker holder.

These and other features of the present subject matter will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
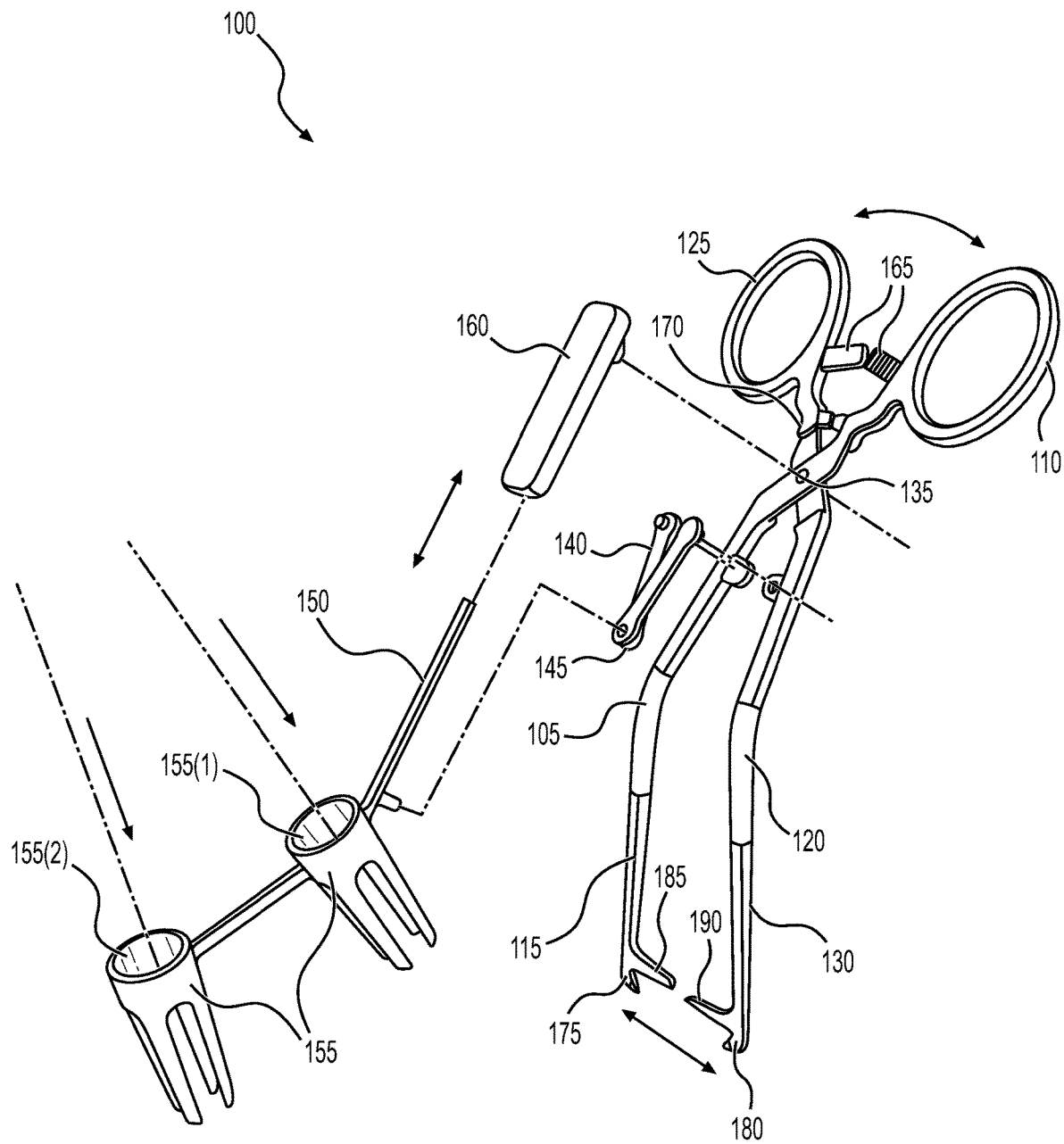
FIG. 1 is an exploded view of a sternal compass.

FIG. 1 is an exploded view of a sternal compass 100 having a first scissor clamp arm 105 having a first scissor clamp arm handle end 110 and a first scissor clamp arm effector end 115; and a second scissor clamp arm 120 having a second scissor clamp arm handle end 125 and second scissor clamp arm effector end 130. The second scissor clamp arm 120 crosses at, and connects to, the first scissor clamp arm 105 at a pivot point 135. A centerline alignment mechanism 140 is located between the first scissor clamp arm 105 and the second scissor clamp arm 120. The centerline alignment mechanism 140 has a hinge point 145 aligned with the pivot point 135. A centerline frame 150 extends in line with the hinge point 145 and the pivot point 135 toward the first scissor clamp arm effector end 115 and the second scissor clamp arm effector end 130. The centerline frame 150 has a marking device 155 to mark a centerline of a sternum.

The centerline alignment mechanism 140 is added to guide the centerline frame 150 to move and position itself at the midline of the sternum.

The sternal compass 100 further includes a finger rest cum centerline guide 160. The centerline frame 150 slides within the finger rest cum centerline guide 160. The finger rest cum centerline guide 160 is attached to the pivot point 135. The centerline frame 150 is connected to the hinge point 145.

The centerline frame 150 is guided by the hinge point 145 of the centerline alignment mechanism 140 and sliding within the finger rest cum centerline guide 160, which in turn is guided at the pivot point 135.

The sternal compass 100 further includes a ratchet lock 165 located between the first scissor clamp arm handle end 110 and the second scissor clamp arm handle end 125.

The sternal compass 100 further includes a stopper 170 located between the first scissor claim arm handle end 110 and the second scissor clamp arm handle end 125.

The first scissor clamp arm effector end 115 includes a first pinching gripper edge 175 and the second scissor clamp arm effector end 130 includes a second pinching gripper edge 180. The pinching gripper edges 175,180 pinch and hinge on either sides of the sternum width. In some embodiments, the pinching gripper edges 175,180 are beveled.

The sternal compass 100 further includes a first depth limiting protrusion 185 located on the first scissor clamp arm effector end 115 above the first pinching gripper edge 175, and a second depth limiting protrusion 190 located on the second scissor clamp arm effector end 130 above the second pinching gripper edge 180. The first depth limiting protrusion 185 and the second depth limiting protrusion 190 prevent the sternal compass 100 from getting below a sternum of a patient thereby protecting internal organs of the patient.

The marking device 155 includes a first collet marker holder 155(1) and a second collet marker holder 155(2) which are used to position and hold tissue marker pens to create markings on the centerline of the sternum. As used herein, "midline" and "centerline" are used interchangeably and refer to the centerline or midline of the sternum.

Figure 2:
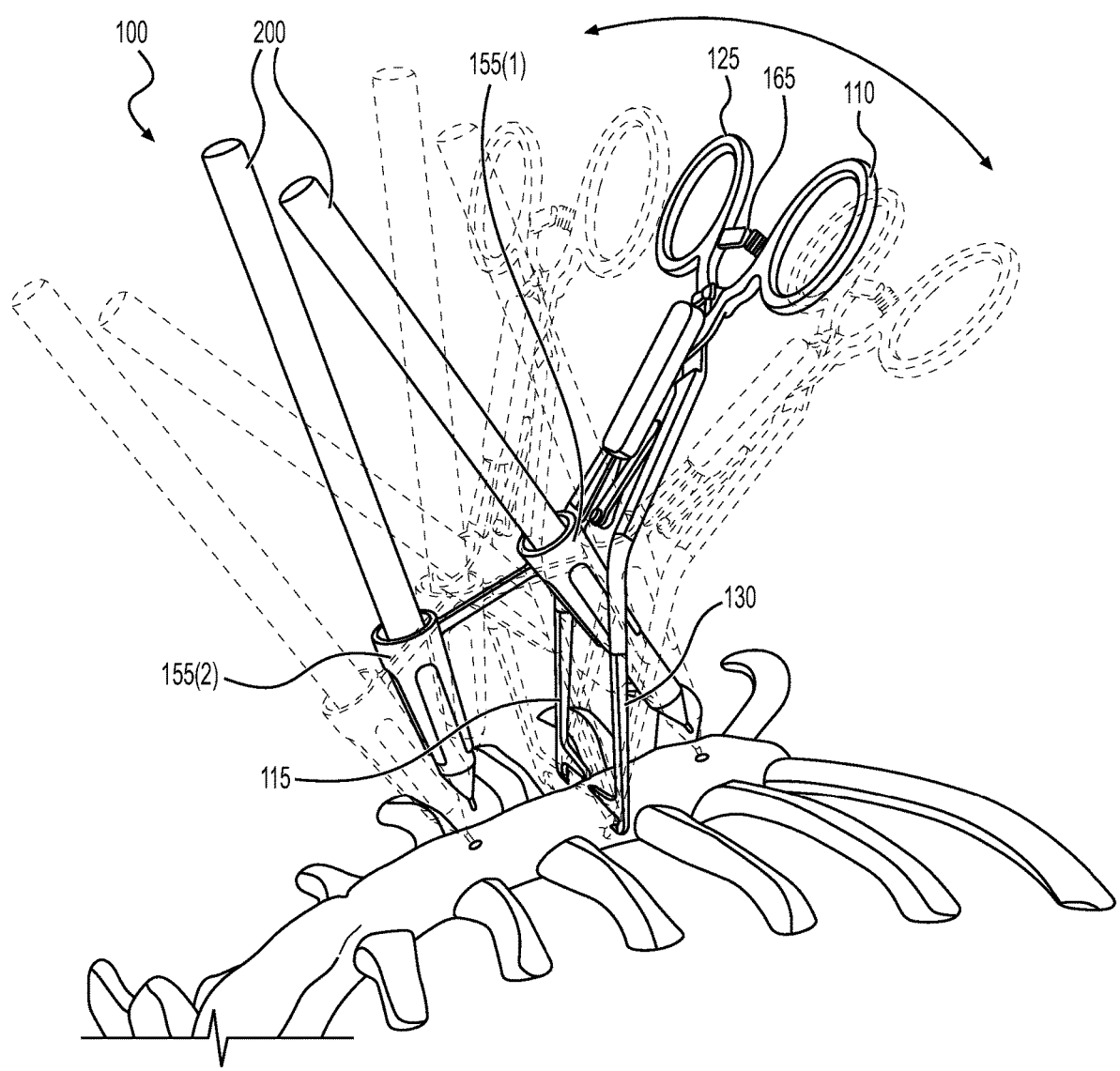
FIG. 2 is an illustration of the sternal compass clamped on a sternum to create marks on the sternum midline.

The sternal compass 100, as illustrated in FIG. 2, is designed to aid in identifying and marking the centerline of a sternum to perform a sternotomy. The ratchet lock 165 is disengaged and the first scissor clamp arm handle end 110 and the second scissor clamp arm handle end 125 are opened by the surgeon with the first scissor clamp arm effector end 115 and the second scissor clamp arm effector end 130 sliding over the sternum of the patient. As the tip reaches the soft tissue at the edge of the sternum, the surgeon pushes on the tool and closes the jaws to pinch and locate the first scissor clamp arm effector end 115 and the second scissor clamp arm effector end 130 on either side of the sternum. The first scissor clamp arm handle end 110 and the second scissor clamp arm handle end 125 are further closed to keep the first scissor clamp arm effector end 115 and the second scissor clamp arm effector end 130 clamped using the ratchet lock 165. In a particular embodiment, the first scissor clamp arm effector end 115 and the second scissor clamp arm effector end 130 are angled at 30 degrees to the first scissor clamp arm handle end 110 and the second scissor clamp arm handle end 125 for a comfortable gripping posture for the surgeon.

Once the sternal compass 100 is clamped in place, the mid points are marked using two centerline markers 200 located in the first collet marker holder 155(1) and the second collet marker holder 155(2), respectively, by swinging the tool forward and backward. Once the mid points are marked, the sternal compass 100 can be unclamped and positioned at another location to make more mid-point marks to guide in marking the center line of the sternum.

Figure 3B:
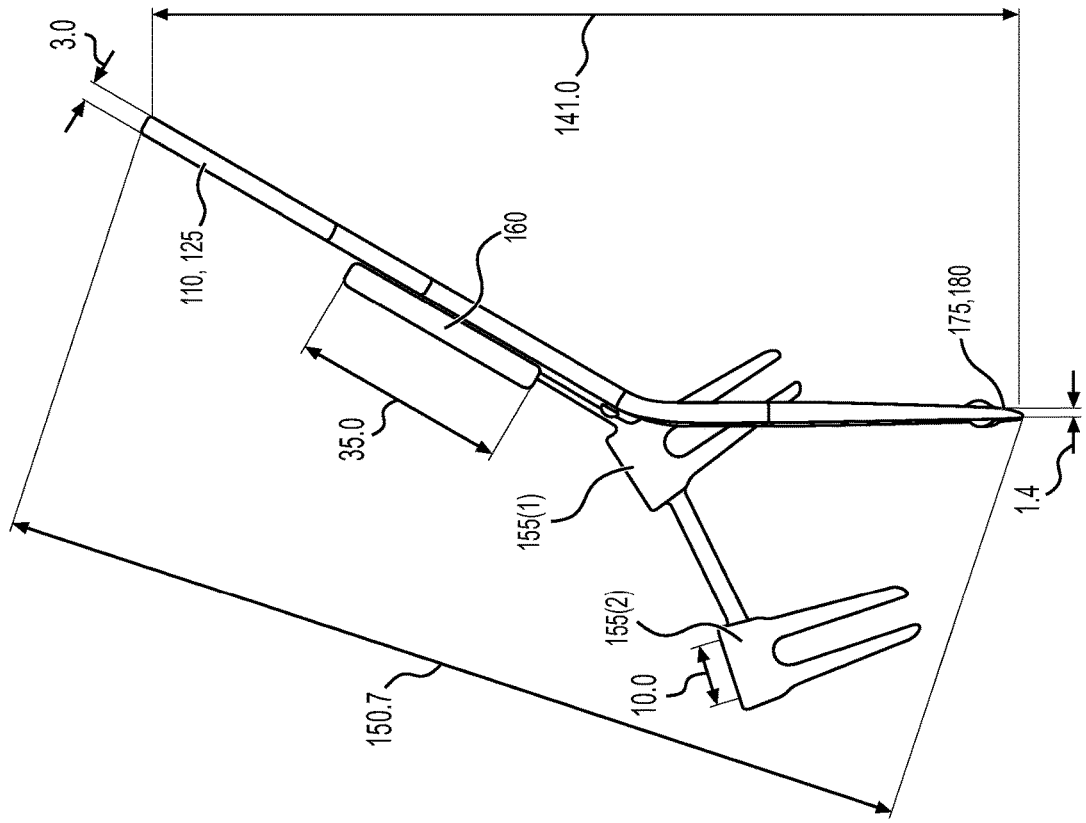
FIGS. 3A and 3B are illustrations showing dimensions of the sternal compass in one embodiment.
Figure 3A:
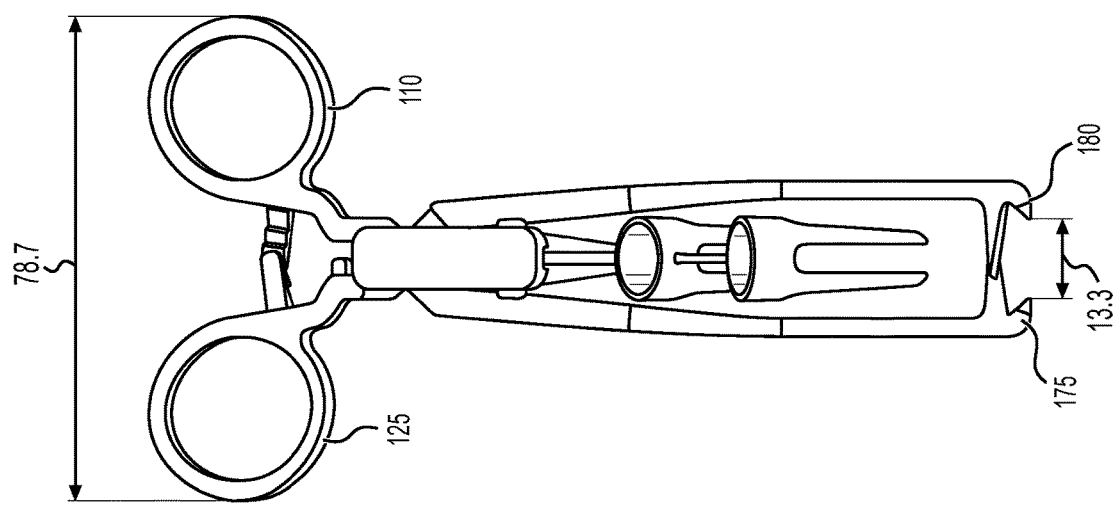

FIGS. 3A and 3B are illustrations showing dimensions of the sternal compass 100 in one non-limiting embodiment. FIG. 3A shows the width of the sternal compass from the first scissor clamp arm handle end 110 and the second scissor clamp arm handle end 125 is 78.7 mm. The distance between the first pinching gripper edge 175 and the second pinching gripper edge 180 is 13.3 mm.

In FIG. 3B the height of the sternal compass is 141 mm. The length of the sternal compass along a hypotenuse is 150.7 mm. The first collet marker holder 155(1) and the second collet marker holder 155(2) each have a diameter of 10 mm. The thickness of each of the first scissor clamp arm handle end 110 and the second scissor clamp arm handle end 125 is 3 mm. The length of the finger rest cum centerline guide 160 is 35 mm. The thickness of the first pinching gripper edge 175 and the second pinching gripper edge 180 is 1.4 mm.

It is to be understood that the sternal compass is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A sternal compass, comprising:
a first scissor clamp arm having a first scissor clamp arm handle end and a first scissor clamp arm effector end;
a second scissor clamp arm having a second scissor clamp arm handle end and a second scissor clamp arm effector end, the second scissor clamp arm crossing the first scissor clamp arm at a pivot point and being pivotally connected thereto;
a centerline alignment mechanism located between the first scissor clamp arm and the second scissor clamp arm, the centerline alignment mechanism having a hinge point aligned with the pivot point, wherein the centerline alignment mechanism comprises first and second elongated members each having first and second ends, the first ends of the first and second elongated members being respectively pivotally connected to the first and second scissor clamp arms, the second ends of the first and second elongated members being pivotally joined to one another at the hinge point, and wherein the hinge point is located closer to the first and second scissor clamp arm effector ends than the pivot point;
a centerline frame extending in line with the hinge point and the pivot point toward the first scissor clamp arm effector end and the second scissor clamp arm effector end, the centerline frame having a marking device to mark a centerline of a sternum.

2. The sternal compass as recited in claim 1, further comprising a finger rest and centerline guide, wherein the centerline frame slides within the finger rest and centerline guide.

3. The sternal compass as recited in claim 2, wherein the finger rest and centerline guide is attached to the pivot point.

4. The sternal compass as recited in claim 1, wherein the centerline frame is connected to the hinge point.

5. The sternal compass as recited in claim 1, further comprising a ratchet lock located between the first scissor clamp arm handle end and the second scissor clamp arm handle end.

6. The sternal compass as recited in claim 1, further comprising a stopper located between the first scissor claim arm handle end and the second scissor clamp arm handle end.

7. The sternal compass as recited in claim 1, wherein the first scissor clamp arm effector end includes a first pinching gripper edge and the second scissor clamp arm effector end includes a second pinching gripper edge.

8. The sternal compass as recited in claim 7, further comprising:
  a first depth limiting protrusion located on the first scissor clamp arm effector end above the first pinching gripper edge; and
  a second depth limiting protrusion located on the second scissor clamp arm effector end above the second pinching gripper edge, wherein the first depth limiting protrusion and the second depth limiting protrusion prevent the sternal compass from moving below a sternum of a patient to protect internal organs of the patient.

9. The sternal compass as recited in claim 1, wherein the marking device includes a collet marker holder.

10. The sternal compass as recited in claim 1, wherein the marking device includes a first collet marker holder and a second collet marker holder.

\* \* \* \* \*